United States Patent [19] [11] Patent Number: 4,568,381
Saito et al. [45] Date of Patent: Feb. 4, 1986

[54] NOVEL HERBICIDALLY ACTIVE SUBSTITUTED PHENYLSULFONYL GUANIDINES AND INTERMEDIATES THEREOF

[75] Inventors: Junichi Saito, Tokyo; Kozo Shiokawa, Kanagawa; Kazuomi Yasui, Tokyo; Atsumi Kamochi, Tokyo; Koichi Moriya, Tokyo; Seishi Ito, Tokyo, all of Japan

[73] Assignee: Nihon Tokushu Noyaku Seizo K.K., Tokyo, Japan

[21] Appl. No.: 621,000

[22] Filed: Jun. 15, 1984

[30] Foreign Application Priority Data

Jun. 24, 1983 [JP] Japan ................... 58-112689

[51] Int. Cl.⁴ ............ C07D 251/46; A01N 43/66; C07D 251/16; C07D 251/22
[52] U.S. Cl. ................................ 71/93; 544/211
[58] Field of Search ................. 544/211; 71/93

[56] References Cited

U.S. PATENT DOCUMENTS 4,453,970  6/1984  Levitt et al. ............ 544/212
4,492,598  1/1985  Willms et al. ........... 544/206

FOREIGN PATENT DOCUMENTS 0005986  12/1979  European Pat. Off.
0043642   1/1982  European Pat. Off.
0056969   8/1982  European Pat. Off.
0074595   3/1983  European Pat. Off.

Primary Examiner—John M. Ford
Attorney, Agent, or Firm—Sprung Horn Kramer & Woods

[57] ABSTRACT

Herbicidally active novel substituted phenylsulfonyl guanidines of the formula

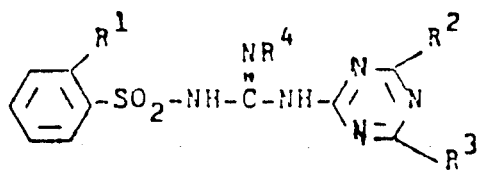

in which
R$^1$ is a phenyl or phenoxy group, each of
R$^2$ and R$^3$ is a lower alkyl or lower alkoxy group, and
R$^4$ is a hydrogen atom, a lower alkyl group or a lower alkoxy group,
and novel intermediates therefor.

6 Claims, No Drawings

NOVEL HERBICIDALLY ACTIVE SUBSTITUTED PHENYLSULFONYL GUANIDINES AND INTERMEDIATES THEREOF

DETAILED DESCRIPTION OF THE INVENTION

This invention relates to novel substituted phenylsulfonyl guanidine derivatives, intermediates thereof, processes for production thereof, and their use as herbicides.

More specifically, this invention relates to substituted phenylsulfonyl guanidine derivatives represented by the following formula (I).

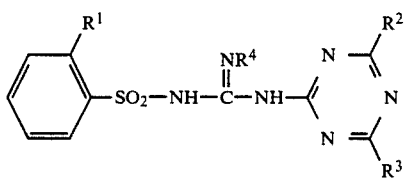

wherein $R^1$ represents a phenyl or phenoxy group, each of $R^2$ and $R^3$ represents a lower alkyl or lower alkoxy group, and $R^4$ represents a hydrogen atom, a lower alkyl group or a lower alkoxy group.

The compounds of the invention represented by general formula (I) can be produced, for example, by the following process (i) to which the invention also pertains:

Process (i)

A process for producing the substituted phenylsulfonyl guanidine derivatives of general formula (I), which comprises reacting a compound represented by the general formula

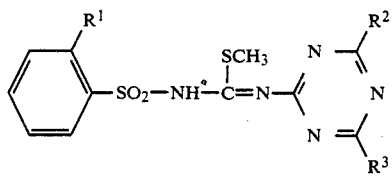

wherein $R^1$, $R^2$ and $R^3$ are as defined above, with a compound of the general formula $$R^4-NH_2 \quad (III)$$

wherein $R^4$ is as defined above.

This invention also relates to substituted phenylsulfonyl isothiourea derivatives of general formula (II) which are intermediates in the process (i) above, and also to the following processes (ii) and (iii) for producing the compounds (II):

Process (ii)

A process for producing the substituted phenylsulfonyl isothiourea derivatives of general formula (II), which comprises reacting a compound of the general formula

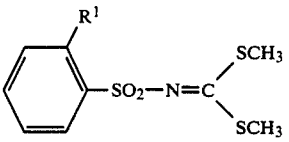

wherein $R^1$ is as defined above, with a compound of the general formula

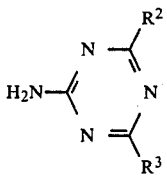

wherein $R^2$ and $R^3$ are as defined above.

Process (iii)

A process for producing the substituted phenylsulfonyl isothiourea derivatives of general formula (II), which comprises reacting a compound of the general formula

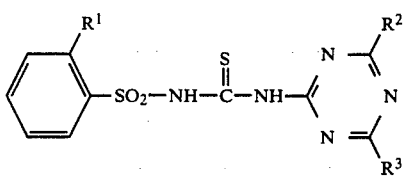

wherein $R^1$, $R^2$ and $R^3$ are as defined, with a methylating agent in the presence of a base.

This invention also relates to substituted phenylsulfonyl thiourea derivatives of general formula (VI) which are intermediates in the process (iii) and the following process (iv) for producing the derivatives of formula (VI):

Process (iv)

A process for producing the substituted phenylsulfonyl thiourea derivatives of general formula (VI), which comprises reacting a compound of the general formula

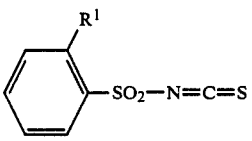

wherein $R^1$ is as defined above, with the compound of general formula (V) given above.

This invention also pertains to substituted benzenesulfonyl isothiocyanates of general formula (VII) which are intermediates in the process (iv), and to the following process (v), for producing the isothiocyanates of general formula (VII):

Process (v)

A process for producing the substituted benzenesulfonyl isothiocyanates of general formula (VII), which comprises reacting a compound of the general formula

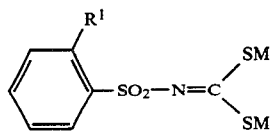

(VIII)

wherein $R^1$ is as defined above and M represents an alkali metal atom, with a compound selected from the group consisting of phosgene, trichloromethyl chloroformate and thionyl chloride.

The present invention further relates to compounds of general formula (IV) which are intermediates in the process (ii), and to the following process (vi) for producing the compounds (IV):

Process (vi)

A process for producing dimethyl N-(substituted phenylsulfonyl)carbonimidodithioates of general formula (IV), which comprises reacting the compound of general formula (VIII) with a methylating agent.

Furthermore, the present invention relates to alkali metal salts of N-(substituted phenylsulfonyl)carbonimidodithioates of general formula (VIII) which are intermediates in the processes (v) and (vi), and the following process (vii) for producing the compounds (VIII):

Process (vii)

A process for producing the alkali metal salts of N-(substituted phenylsulfonyl)carbonimidodithioates represented by general formula (VIII), which comprises reacting a compound of the general formula

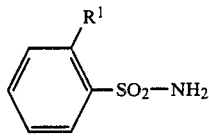

(IX)

wherein $R^1$ is as defined above, with carbon disulfide and a compound of the general formula

MOH    (X)

wherein M is as defined above.

This invention also relates to a herbicide comprising the substitute phenylsulfonyl guanidine derivative of general formula (I) as an active ingredient.

The novel substituted phenylsulfonyl guanidine derivatives of general formula (I) exhibit excellent herbicidal activity. It has also been found that when these compounds are used as herbicides for aquatic paddies, they show an outstanding selective herbicidal effect against paddy weeds without causing phytotoxicity to rice plants.

The compounds of general formulae (II), (IV), (VI), (VII), (IX) and (X), which are intermediates for the production of the substituted phenylsulfonyl guanidine derivatives of general formula (I), are also quite novel compounds not described in the prior literature. Among these intermediates, the substituted phenylsulfonyl isothiourea derivatives of general formula (II) and the substituted phenylsulfonyl thiourea derivatives of general formula (VI) have excellent herbicidal activity by themselves, and are useful not only as intermediates for production of other useful compounds but also as herbicides.

It is an object of this invention therefore to provide substituted phenylsulfonyl guanidine derivatives of general formula (I), intermediates therefor, processes for production thereof, and use thereof as herbicides, particularly as selective herbicides against aquatic paddy weeds.

The above and other objects and advantages of this invention will become more apparent from the following description.

The compounds of this invention show an outstanding selective control effect when used as a pre-emergence soil treating agent or a stalk foliar/soil treating agent against aquatic paddy weeds.

The compounds of this invention have high safety, outstanding herbicidal activity and a broad herbicidal spectrum.

For example, they are characterized by having herbicidal activity against the following aquatic paddy weeds without any phytotoxicity to rice.

| Plant name | Latin scientific name |
| --- | --- |
| Dicotyledons | |
| Kikashigusa | *Rotala indica* Koehne |
| False pimpernel | *Lindernia procumbens* Philcox |
| False loosestrife | *Ludwigia prostrata* Roxburgh |
| Largeleaf pondweed | *Potamogeton distinctus* A. Bennett |
| American watarwort | *Elatine triandra* Schkuhr |
| Monocotyledons | |
| Barnyard grass | *Echinochloa crus-galli* Beauv. var |
| Monochria | *Monochoria vaginalis* Presl |
| Spikerush | *Eleocharis acicularis* L. |
| Water chestnut | *Eleocharis Kuroguwai* Ohwi |
| Umbrella plant | *Cyperus difformis* L. |
| Mizugayatsuri | *Cyprus serotinus* Rottboel |
| Urikawa | *Sagittaria pygmaea* Miq. |
| Narrowleaf waterplantain | *Alisma canaliculatum* A. Br. et Boucha |
| Bulrush | *Scirpus juncoides* Roxburgh var. |

Furthermore, they are characterized by having herbicidal activity against the following upland farm weeds:

| Plant name | Latin scientific name |
| --- | --- |
| Dicotyledons | |
| Tade | *Polygonum sp.* |
| Goosefoot | *Chenopodium album* Linnacus |
| Common chickweed | *Stellaria media* Villars |
| Common purslane | *Portulaca oleraca* Limnaous |
| Monocotyledons | |
| Barnyard grass | *Echinochloa crus-galli* Beauv. var. |
| Fingergrass | *Digitaria adscendens* Henr. |
| Chufa | *Cyperus microiria* |

They are further characterized by causing no phytotoxicity to such upland farm crops as mustards, cotton, carrot, beans, potato, beat and cabbage (dicotyledons); and corn, rice, oat, barley, wheat, *Panicum milliaceum* and *Saccharum officinarum* (monocotyledons).

It should be understood that the plant names given above are typical examples of each of the genera written in Latin scientific names.

The applicability of the active compounds of this invention is not limited to weeds in aquatic paddies and upland farms. They are also effective against weeds noxious to mat rush (*Juncus effusus* Linnaeus var. decipiens Buchanan), weeds occurring in lands which are temporarily out of cultivation, etc. The term "weeds", as used herein, means all plants which occur in undesired sites in the broadest sense.

The substituted phenylsulfonyl guanidine derivatives of this invention represented by general formula (I) can be synthesized, for example, by the following process (i).

Process (i)

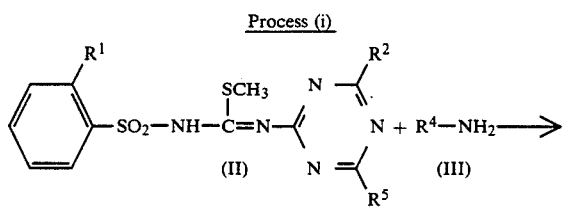

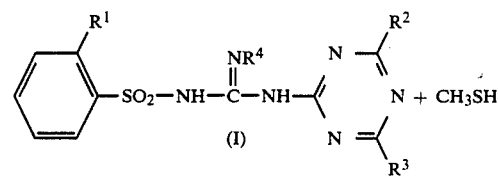

In the formulae, $R^1$, $R^2$, $R^3$ and $R^4$ are as defined above.

In the above reaction scheme:
$R^1$ represents a phenyl or phenoxy group;
each of $R^2$ and $R^3$ represents a lower alkyl group or a lower alkoxy group, specifically such lower alkyl groups as methyl, ethyl, propyl, isopropyl, and n-(iso-,sec-, or tert-)butyl, and lower alkoxy groups having the same lower alkyl groups as above; and
$R^4$ represents a hydrogen atom, a lower alkyl group, or a lower alkoxy group, specific examples of the lower alkyl and lower alkoxy groups being the same as given above with regard to $R^2$ and $R^3$.

In the process for producing the substituted phenylsulfonyl guanidine derivatives of general formula (I) shown by the above reaction scheme, specific examples of the starting compound of general formula (II) include:

1-(2-biphenylylsulfonyl) 3-(4-methoxy-6-methyl-1,3,5-triazin-2-yl) 2-methylisothiourea,
1-(2-biphenylylsulfonyl) 3-(4,6-dimethoxy-1,3,5-triazin-2-yl) 2-methylisothiourea,
3-(4,6-dimethoxy-1,3,5-triazin-2-yl) 2-methyl-1-(2-phenoxysulfonyl)isothiourea, and
3-(4-methoxy-6-methyl-1,3,5-triazin-2-yl) 2-methyl 1-(2-phenoxyphenylsulfonyl)isothiourea.

Likewise, specific examples of the starting compound of general formula (III) are ammonia, O-methylhydroxylamine, methylamine and O-propylhydroxylamine.

The above process is specifically illustrated by citing the following typical example:

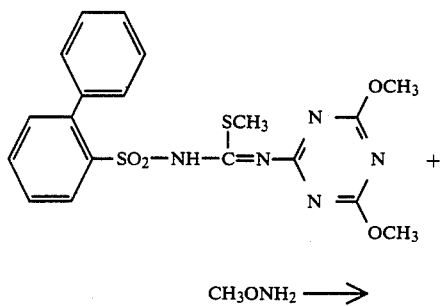

CH₃ONH₂ ⟶

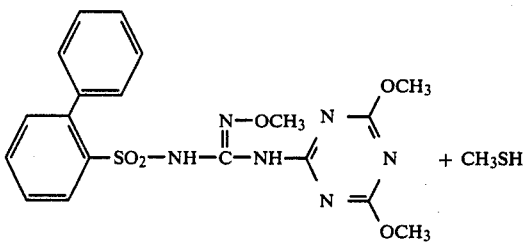

The above process for producing the compounds of this invention can be carried out, desirably in a solvent or diluent. For this purpose, all inert solvents and diluents can be used.

Examples of such solvents or diluents include aliphatic, alicyclic and aromatic hydrocarbons (which may optionally be chlorinated) such as hexane, cyclohexane, petroleum ether, ligroin, benzene, toluene, xylene, methylene chloride, chloroform, carbon tetrachloride, ethylene chloride, trichloroethylene and chlorobenzene; ethers such as diethyl ether, methyl ethyl ether, di-isopropyl ether, dibutyl ether, propylene oxide, dioxane and tetrahydrofuran; ketones such as acetone, methyl ethyl ketone, methyl isopropyl ketone and methyl isobutyl ketone; nitriles such as acetonitrile, propionitrile and acrylonitrile; esters such as ethyl acetate and amyl acetate; acid amides such as dimethylformamide and dimethylacetamide; sulfones and sulfoxides such as dimethyl sulfoxide and sulfolane; and bases such as pyridine.

The above process of this invention can be carried out over a broad temperature range, generally at a temperature between $-20°$ C. and the boiling point of the mixture, desirably at a temperature between about $0°$ C. and about $100°$ C. Desirably, the reaction is carried out under atmospheric pressure, but it is also possible to operate under elevated or reduced pressures.

The substituted phenylsulfonyl isothiourea derivative of general formula (II) which is an intermediate can be produced, for example, by the following process (ii) or (iii):

Process (ii)

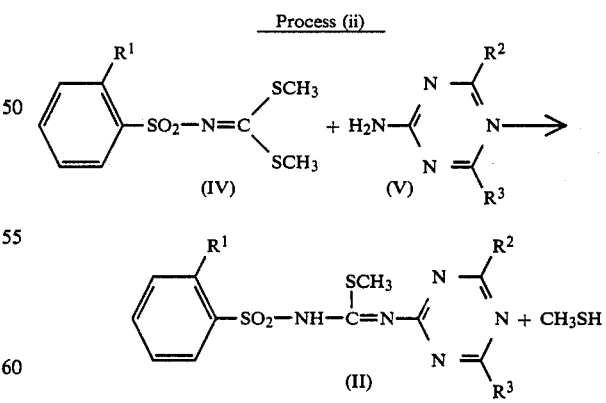

In the formulae, $R^1$, $R^2$ and $R^3$ are as defined hereinabove.

In the process for producing the substituted phenylsulfonyl isothiourea derivative of general formula (II) shown by the above reaction scheme, specific examples of the starting compound of general formula (IV) are dimethyl N-(2-biphenylylsulfonyl)carbonimidodithioate, and dimethyl N-(2-phenoxyphenylsulfonyl)carbonimidodithioate.

Likewise, specific examples of the starting compound of general formula (V) are 2-amino-4,6-dimethoxy-1,3,5-triazine, 2-amino-4-methoxy-6-methyl-1,3,5-triazine, and 2-amino-4,6-dimethyl-1,3,5-triazine.

The above process is specifically illustrated by citing the following typical example:

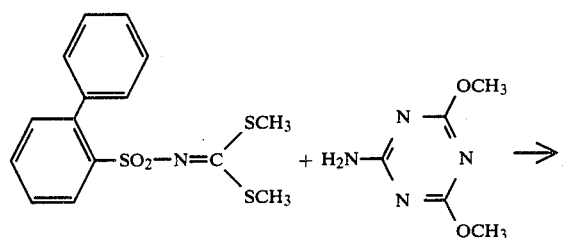

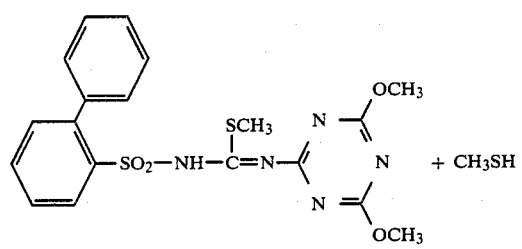

By performing the above process preferably using the same inert solvent or diluent as above, the desired product of high purity can be obtained in a high yield.

The above process can also be carried out efficiently in the presence of, for example, sodium hydride or potassium hydride.

The above reaction can be performed over a wide temperature range, for example, at a temperature between about −20° C. to the boiling point of the mixture, preferably between about 0° and about 100° C. Preferably, the reaction is carried out under atmospheric pressure, but it is also possible to operate under elevated or reduced pressures.

Process (iii)

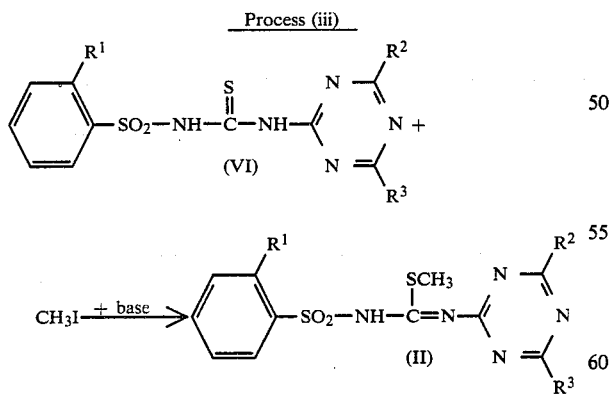

In the formulae, $R^1$, $R^2$ and $R^3$ are as defined above.

In the process for producing the substituted phenylsulfonyl isothiourea derivatives of general formula (II) shown by the above reaction scheme, specific examples of the starting compound of general formula (VI) include:

1-(2-biphenylylsulfonyl) 3-(4-methoxy-6-methyl-1,3,5-triazin-2-yl)thiourea, 1-(2-biphenylylsulfonyl) 3-(4,6-dimethoxy-1,3,5-triazin-2-yl)thiourea, 3-(4,6-dimethoxy-1,3,5-triazin-2-yl) 1-(2-phenoxyphenylsulfonyl)thiourea, and 3-(4-methoxy-6-methyl-1,3,5-triazin-2-yl) 1-(2-phenoxyphenylsulfonyl)thiourea.

Examples of the methylating agent are methyl iodide, dimethyl sulfate, methyl bromide and methyl chloride.

The above process should be carried out in the presence of a base. Examples of the base are metallic sodium, metallic potassium, metallic lithium, sodium hydroxide, potassium hydroxide and lithium hydroxide.

The above process is illustrated specifically by citing the following typical example:

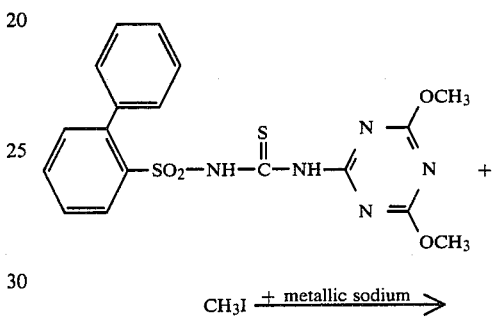

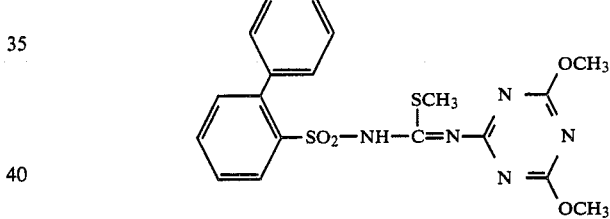

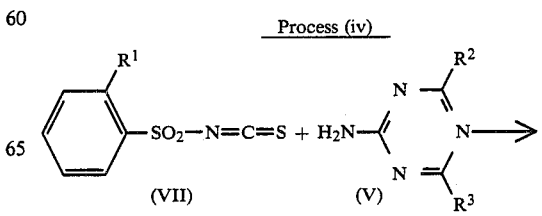

The above process is carried out preferably by using the same inert solvent or diluent as described hereinabove to give the desired product of high purity in a high yield.

The above reaction can be carried out over a wide temperature range, for example, at a temperature between about −20° C. and the boiling point of the mixture, preferably between about 0° and about 100° C. Preferably, the reaction is carried out under atmospheric pressure, but it is also possible to operate under elevated or reduced pressure.

The substituted phenyl sulfonyl thiourea derivatives of general formula (VI) which are intermediates can be synthesized, for example, by the following process (iv).

Process (iv)

-continued
Process (iv)

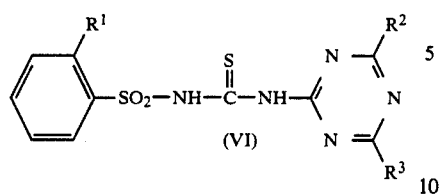
(VI)

In the formulae, R¹, R² and R³ are as defined above.

In the process for producing the substituted phenylsulfonyl thiourea derivatives of general formula (VI) shown by the above reaction scheme, specific examples of the starting compound of general formula (VII) are 2-phenylbenzenesulfonyl isothiocyanate and 2-phenoxybenzenesulfonyl isothiocyanate.

Specific examples of the starting compound of general formula (V) may be the same as those given with regard to process (ii).

The above process is illustrated specifically by citing the following typical example.

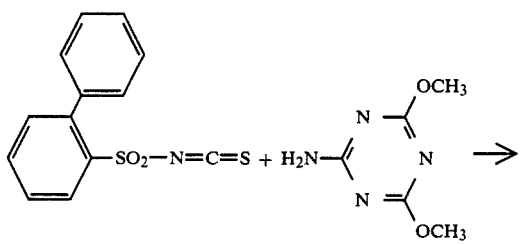

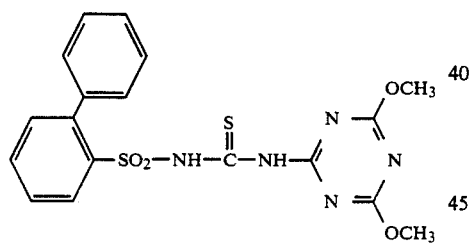

The above process is performed preferably by using the same inert solvent or diluent as described hereinabove to give the desired product of high purity in a high yield.

The above reaction can be carried out over a wide temperature range, for example at a temperature between about −20° C. and the boiling point of the mixture, preferably between about 0° to about 100° C. The reaction is carried out preferably under atmospheric pressure, but it is also possible to operate under reduced or elevated pressures.

The reaction can be promoted by using an organic base such as triethylamine and diazabicyclooctane as a catalyst.

The substituted benzenesulfonyl isothiocyanates of general formula (VII) which are intermediates can be synthesized, for example, by the following process (v).

Process (v)

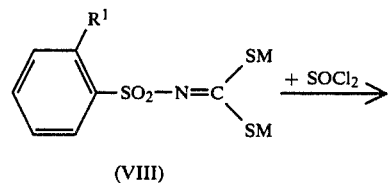
(VIII)

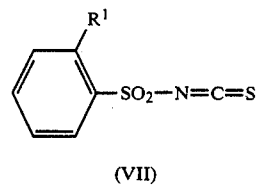
(VII)

In the formulae, R¹ and M are as defined above.

In the process for producing the substituted benzenesulfonyl isothiocyanates of general formula (VII) shown by the above reaction scheme, specific examples of the compound of general formula (VIII) are potassium N-(2-biphenylylsulfonyl)carbonimidodithioate, and potassium N-(2-phenoxyphenylsulfonyl)carbonimidodithioate. Instead of the potassium salts, the corresponding salts of other alkali metals such as sodium and lithium may also be used.

Likewise, phosgene or trichloromethyl chloroform may be reacted instead of the starting thionyl chloride.

The above process is specifically illustrated by citing the following typical example:

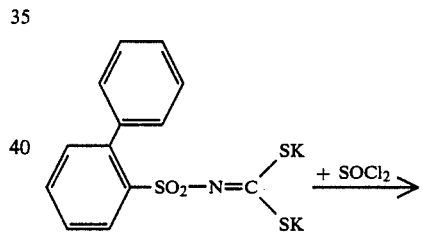

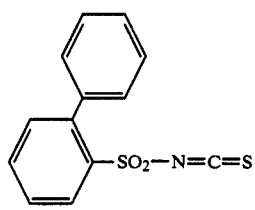

The above process is carried out preferably by using the same inert solvent or diluent as described above to give the desired product of high purity in a high yield.

The above reaction can be carried out over a wide temperature range, for example at a temperature between about −20° C. and the boiling point of the mixture, preferably between about 0° and about 100° C. The reaction is carried out preferably under atmospheric pressure, but it is also possible to operate under elevated or reduced pressures.

The dimethyl N-(substituted phenylsulfonyl)carbonimidodithioates of general formula (IV) which are intermediates can be synthesized, for example, by the following process (vi):

Process (vi)

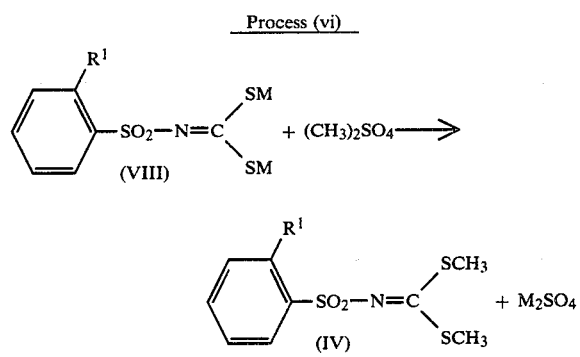

In the formulae, $R^1$ and M are as defined above.

In the process for producing the dimethyl N-(substituted phenylsulfonyl)carbonimidodithioates of general formula (IV) shown by the above reaction scheme, specific examples of the compound of formula (VIII) may be the same as those given with regard to process (v).

Examples of the methylating agent may be those given hereinabove with regard to process (iii) in addition to dimethyl sulfate shown in the above reaction scheme.

The above process is illustrated specifically by citing the following typical example:

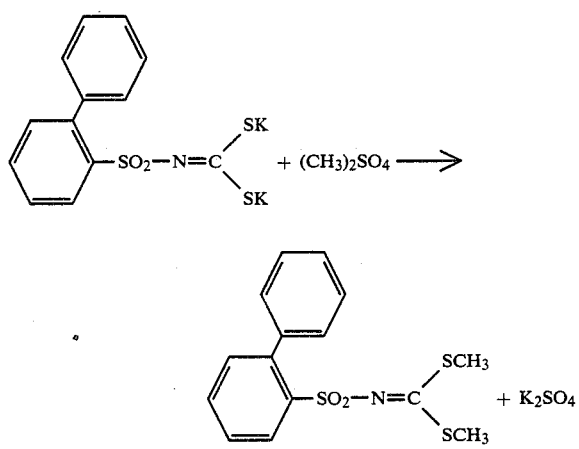

The above process is carried out preferably by using the same inert solvent or diluent as described hereinabove to give the desired product of high purity in a high yield.

The above reaction can be carried out over a wide temperature range, for example at a temperature between about $-20°$ C. and the boiling point of the mixture, preferably between about 0° and about 100° C. The reaction is carried out preferably under atmospheric pressure, but it is also possible to operate under elevated or reduced pressures.

The alkali metal salts of N-(substituted phenylsulfonyl)carbonimidodithioates of general formula (VIII) which are intermediates can be synthesized, for example, by the following process (vii).

Process (vii)

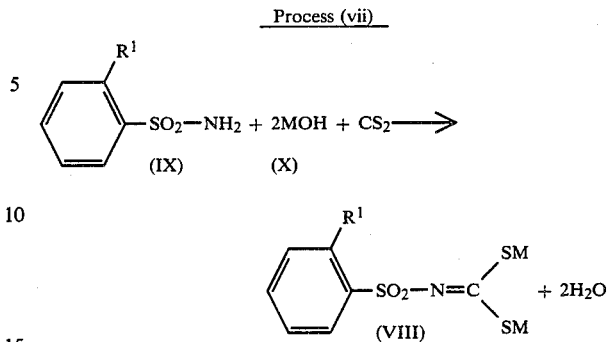

In the above formulae, $R^1$ and M are as defined above.

In the process for producing the alkali salts of the N-(substituted phenylsulfonyl)carbonimidodithioates of general formula (VIII), specific examples of the starting compound of general formula (IX) are 2-phenylbenzenesulfonamide and 2-phenoxybenzenesulfonamide.

Likewise, specific examples of the starting compound of general formula (X) are potassium hydroxide, sodium hydroxide and lithium hydroxide.

The above process is illustrated specifically by citing the following typical example.

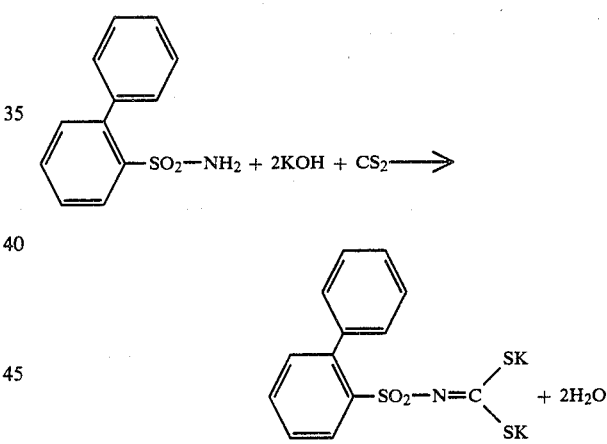

The above process is carried out preferably by using the same inert solvent or diluent as described above to give the desired compound of high purity in a high yield.

The above reaction can be carried out over a wide temperature range, for example at a temperature between about $-20°$ C. and the boiling point of the mixture, preferably between about 0° and about 100° C. The reaction is carried out preferably under atmospheric pressure but it is also possible to operate under elevated or reduced pressures.

The substituted phenylsulfonyl guanidine derivatives of general formula (I) in accordance with this invention can also be produced by starting with the process (vii) above as a first-stage reaction, and without separating the intermediates, performing the above reactions successively. The overall synthesis is schematically shown as follows:

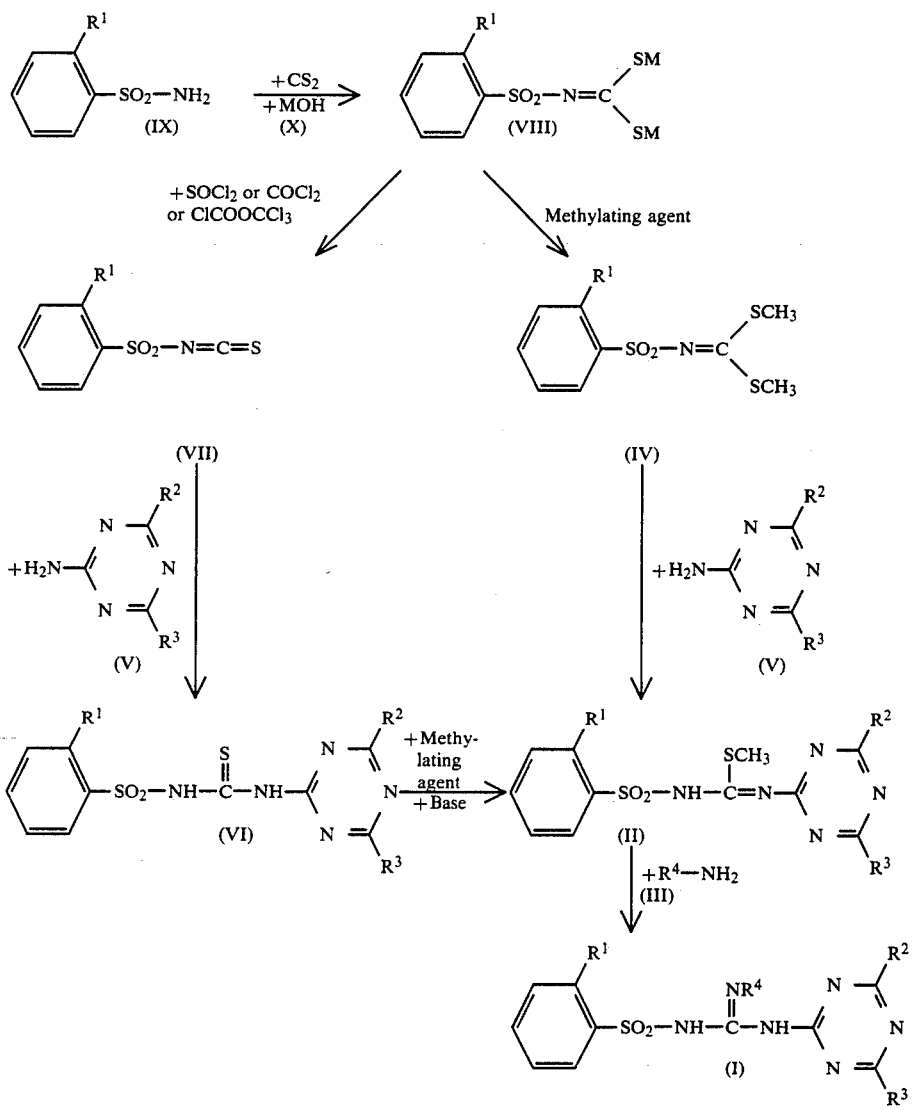

For use as a herbicide, the compounds of this invention represented by general formula (I) may be used as such after diluting them directly with water, or after formulating them into various forms using agriculturally acceptable adjuvants by methods generally practiced in the production of agricultural chemicals. In actual use, the herbicidal compositions in various forms are applied either directly or after diluting them with water to the desired concentrations. Examples of the agriculturally acceptable adjuvants, as referred to herein, are diluents (solvents, extenders, carriers), surface-active agents (solubilizing agents, emulsifiers, dispersants, wetting agents), stabilizers, stickers, aerosol propellants, and synergists.

Examples of the solvents are water, and organic solvents, for example hydrocarbons [(e.g., n-hexane, petroleum ether, naphtha, petroleum fractions (e.g., paraffin waxes, kerosene, light oils, middle oils, heavy oils), benzene, toluene, and xylenes], halogenated hydrocarbons [e.g., methylene chloride, carbon tetrachloride, trichloroethylene, ethylene chloride, ethylene dichloride, chlorobenzene and chloroform], alcohols [e.g., methyl alcohol, ethyl alcohol, propyl alcohol, and ethylene glycol], ethers [e.g., ethyl ether, ethylene oxide and dioxane], alcohol ethers [e.g., ethylene glycol monomethyl ether], ketones [e.g., acetone and isophorone], esters [e.g., ethyl acetate and amyl acetate], amides [e.g., dimethylformamide and dimethylacetamide] and sulfoxides [e.g., dimethyl sulfoxide].

Examples of the extenders or carriers include inorganic powders, for example sulfur, slaked lime, magnesium lime, gypsum, calcium carbonate, silica, perlite, pumice, calcite, diatomaceous earth, amorphous silica, alumina, zeolites, and clay minerals) e.g., pyrophyllite, talc, montmorillonite, beidellite, vermiculite, kaolinite and mica); vegetable powders such as cereal powders, starches, processed starches, sugar, glucose and crushed stalks of plants; and powders of synthetic resins such as phenolic resins, urea resins, and vinyl chloride resins.

Examples of the surface-active agents include anionic surface-active agents such as alkylsulfuric acid esters (e.g., sodium laurylsulfate), arylsulfonic acid salts (e.g., alkylarylsulfonic acid salts and sodium alkylnaphthalenesulfonates), succinic acid salts and salts of sulfuric acid esters of polyethylene glycol alkylaryl ethers; cationic surface-active agents such as alkylamines (e.g., laurylamine, stearyl trimethyl ammonium chloride and alkyl dimethylbenzyl ammonium chloride) and polyoxyethylene alkylamines; nonionic surface-active agents such as polyoxyethylene glycol ethers (e.g., polyoxyethylene alkylaryl ethers and the condensation products thereof), polyoxyethylene glycol esters (e.g., polyoxyethylene fatty acid esters), and polyhydric alcohol esters (e.g., polyoxyethylene sorbitan monolaurate); and amphoteric surface-active agents.

Examples of other adjuvants include stabilizers; stickers (e.g., agricultural soaps, casein lime, sodium alginate, polyvinyl alcohol, vinyl acetate-type adhesives and acrylic adhesives); effect-prolonging agents; dispersion stabilizers (e.g., casein, tragacanth, carboxymethyl cellulose and polyvinyl alcohol); and synergists.

The compounds of this invention can be formulated onto various forms by methods generally practiced in the field of manufacturing agricultural chemicals. Examples of the forms include emulsifiable concentrates, oils, wettable powders, soluble powders, suspensions, dusts, granules, pulverulent compositions and capsules.

The herbicidal compositions of this invention may contain about 0.001 to about 100% by weight, preferably about 0.005 to about 95% by weight, of the aforesaid active ingredients.

In actual use, the suitable amount of the active compound in the aforesaid compositions in various forms and ready-to-use preparations is, for example, about 0.01 to about 95% by weight, preferably about 0.05 to about 60% by weight.

The content of the active ingredient can be properly varied depending upon the form of the preparation or composition, the method, purpose, time and locus of its application, the state of occurrence of weeds, etc.

If required, the compounds of this invention may be used further in combination with other agricultural chemicals, for example insecticides, fungicides, miticides, nematocides, antiviral agents, other herbicides, plant growth regulators and attractants [e.g., organophosphorus ester compounds, carbamate compounds, dithio (or thiol) carbamate compounds, organic chlorine compounds, dinitro compounds, organic sulfur or metal compounds, antibiotics, substituted diphenyl ether compounds, urea compounds, and triazine compounds], and/or fertilizers.

Various compositions and ready-to-use preparations containing the aforesaid active ingredients of the invention can be applied by various methods generally practiced in the field of agricultural chemical application, for example spraying (liquid spraying, misting, atomizing, dust scattering, granule scattering, water surface application and pouring); and soil application (mixing with the soil, and sprinkling). They can also be used by the so-called ultralow volume spraying method. According to this method, the active ingredient may be included in an amount of 100%.

The rates of application per unit area is, for example, about 0.1 to about 3.0 kg, preferably about 0.2 to about 1 kg, per hectare. In special cases, however, it may, and sometimes should, be outside the specified range.

According to this invention, there is provided a herbicidal composition comprising a compound of general formula (I) as an active ingredient and a diluent (a solvent and/or an extender and/or a carrier) and/or a surface-active agent, and if further required, a stabilizer, a sticker, a synergist, etc.

The invention also provides a method for controlling weeds, which comprises applying to weeds and/or their habitat the compound of general formula (I) alone or in admixture with a diluent (a solvent and/or an extender and/or a carrier) and/or a surface active agent and if required, a stabilizer, a sticker, a synergist, etc.

The following examples illustrate the present invention specifically. It should be noted however that the invention is not limited to these specific examples alone.

EXAMPLE 1

Synthesis of an intermediate of general formula (VIII)

115.5 g of 2-phenylbenzenesulfonamide were dissolved in 500 ml of dimethylformamide, and 38 g of carbon disulfide and 28 g of potassium hydroxide were added to the resulting solution. The mixture was stirred at room temperature for 7 hours. Potassium hydroxide (28 g) was added to the reaction mixture, and the mixture was stirred at room temperature for 2 hours. Then, 400 ml of ethyl acetate were added dropwise to precipitate pale yellow crystals. The crystals were filtered, and washed with ethyl acetate to give 160 g of potassium N-(2-biphenylylsulfonyl)carbonimidodithioate represented by the following formula:

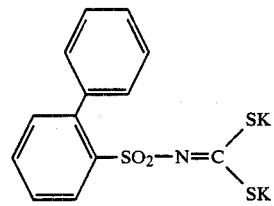

(Compound No. VIII-1)

By the same procedure as in Example 1 above, potassium N-(2-phenoxyphenylsulfonyl)carbonimidodithioate (Compound No. VIII-2) was synthesized.

EXAMPLE 2

Synthesis of an intermediate of general formula (IV)

77 g of potassium N-(2-biphenylylsulfonyl)carbonimidodithioate were dissolved in 200 ml of dimethylformamide, and 50.4 g of dimethyl sulfate were added dropwise to the solution at 60° C. over the course of 1 hour. After the addition, the mixture was heated to 70°-80° C. for 2 hours. After cooling, the reaction mixture was poured into 1 liter of water. The precipitated crystals were collected by filtration to give 65 g of dimethyl N-(2-biphenylylsulfonyl)carbonimidodithioate of the following formula:

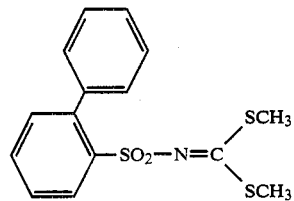

(Compound No. IV-1)

Melting point: 115°-117° C.

By substantially the same procedure as in Example 2 above, dimethyl N-(2-phenoxyphenylsulfonyl)carbonimidodithioate (compound No. IV-2) was synthesized.

EXAMPLE 3

Synthesis of an intermediate of general formula (VII)

77 g of potassium N-(2-biphenylylsulfonyl)carbonimidodithioate were suspended in 100 ml of toluene, and 37 ml of thionyl chloride were added dropwise at 0° to 10° C. over the course of 1 hour. After the addition, the mixture was stirred at room temperature for 2 hours. The reaction mixture was filtered, and the filtrate was concentrated under reduced pressure and distilled under reduces pressure to give 30 g of 2-phenylbenzenesulfonyl isothiocyanate represented by the following formula:

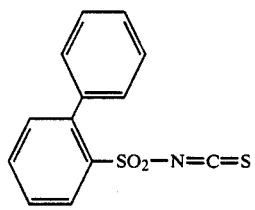

(Compound No. VII-1)

Boiling point: 170° C./0.5 mmHg

In substantially the same way as in Example 3 above, 2-phenoxybenzenesulfonyl isothiocyanate (compound No. VII-2) was synthesized.

EXAMPLE 4

Synthesis of an intermediate of general formula (VI)

15.6 g of 2-amino-4,6-dimethoxy-1,3,5-triazine were suspended in 300 ml of dry toluene, and 27.5 g of 2-phenylbenzenesulfonyl isothiocyanate were added. The mixture was heated under reflux for 8 hours. After cooling, the resulting precipitate was collected by filtration and recrystallized from ethanol to give 35 g of 1-(2-biphenylylsulfonyl) 3-(4,6-dimethoxy-1,3,5-triazin-2-yl)thiourea represented by the following formula:

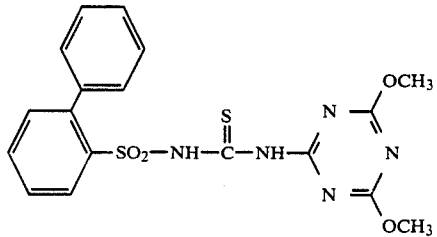

(Compound No. VI-1)

Melting point: 192°–193° C.

By substantially the same procedure as in Example 4 above the following compounds were synthesized:
Compound No. VI-2: 1-(2-biphenylylsulfonyl) 3-(4-methoxy-6-methyl-1,3,5-triazin-2-yl)thiourea
Compound No. VI-3: 3-(4,6-dimethoxy-1,3,5-triazin-2-yl) 1-(2-phenoxyphenylsulfonyl)thiourea
Compound No. VI-4: 3-(4-methoxy-6-methyl-1,3,5-triazin-2-yl) 1-(2-phenoxyphenylsulfonyl)thiourea

EXAMPLE 5

Synthesis of an intermediate of general formula (II)

4.31 g of 1-(2-biphenylylsulfonyl) 3-(4,6-dimethoxy-1,3,5-triazin-2-yl)thiourea were suspended in 50 ml of dry acetonitrile, and a solution of 0.3 g of metallic sodium in 10 ml of ethanol was added to the suspension, and the mixture was heated under reflux for 30 minutes. After cooling, 1.85 g of methyl iodide were added, and the mixture was heated under reflux for 5 hours. After cooling, the reaction mixture was poured into 100 ml of water, and extracted with methylene chloride. Methylene chloride was distilled off under reduced pressure from the extract, and the residue was recrystallized from ethanol to give 2.1 g of 1-(2-biphenylylsulfonyl) 3-(4,6-dimethoxy-1,3,5-triazin-2-yl) 2-methylisothiourea represented by the following formula:

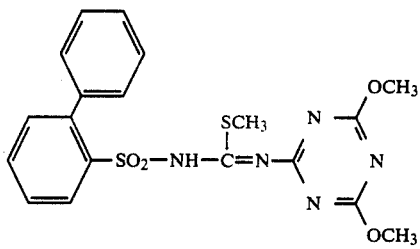

(Compound No. II-1)

Melting point: 135° to 137° C.

By substantially the same procedure as in Example 5 above, the following compounds were synthesized
Compound No. II-2: 1-(2-biphenylylsulfonyl) 3-(4-methoxy-6-methyl-1,3,5-triazin-2-yl) 2-methylisothiourea
Compound No. II-3: 3-(4,6-dimethoxy-1,3,5-triazin-2-yl) 2-methyl 1-(2-phenoxyphenylsulfonyl)isothiourea
Compound No. II-4: 3-(4-methoxy-6-methyl-1,3,5-triazin-2-yl) 2-methyl 1-(2-phenoxyphenylsulfonyl)isothiourea

EXAMPLE 6

Synthesis of an intermediate of general formula (II)

15.6 g of 2-amino-4,6-dimethoxy-1,3,5-triazine were suspended in 300 ml of dimethylformamide, and 4 g of sodium hydride (oily, 60%) were added to the suspension. The mixture was stirred at room temperature for 1 hour. Furthermore, 33.7 g of dimethyl N-(2-biphenylylsulfonyl)carbonimidodithioate were added, and the mixture was stirred at room temperature for a day and night. The reaction mixture was poured into 2 liters of water and filtered. The filtrate was made weakly acidic to precipitate white crystals. The crystals were collected by filtration and recrystallized from ethanol to give 36.2 g of 1-(2-biphenylylsulfonyl) 3-(4,6-dimethoxy-1,3,5-triazin-2-yl) 2-methylisothiourea (compound No. II-1), the same compound as obtained in Example 5. The melting point of the product was 135° to 137° C.

It was confirmed that by substantially the same procedure as in Example 6 above, compounds Nos. II-2, II-3 and II-4 could be easily synthesized.

EXAMPLE 7

Synthesis of the final compound of general formula (I)

4.45 g of 1-(2-biphenylylsulfonyl) 3-(4,6-dimethoxy-1,3,5-triazin-2-yl) 2-methylisothiourea were dissolved in 50 ml of dioxane, and 2.35 g of O-methylhydroxylamine were added to the solution. The mixture was heated under reflux for 5 hours. After cooling, the solvent was distilled off under reduced pressure, and the residue was recrystallized from ethanol to give 3.1 g of N-(2-biphenylylsulfonyl) N'-(4,6-dimethoxy-1,3,5-triazin-2-yl) N''-(methoxy)guanidine represented by the following formula:

(Compound No. I-1)

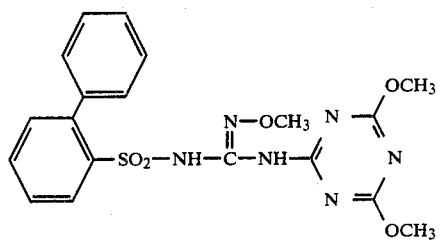

Melting point: 189° to 190.5° C.

By substantially the same procedure as in Example 7 above, the compounds shown in Table 1 were synthesized.

TABLE 1

| Compound No. | Structure | mp. |
|---|---|---|
| I-2 | [biphenyl-SO₂—NH—C(=N—CH₃)—NH—(triazine with 2 OCH₃)] | 164–167° C. |
| I-3 | [biphenyl-SO₂—NH—C(=N—OCH₃)—NH—(triazine with OCH₃ and CH₃)] | 138–141° C. |
| I-4 | [biphenyl-SO₂—NH—C(=N—OC₃H₇-n)—NH—(triazine with 2 OCH₃)] | 157–162° C. |
| I-5 | [phenoxyphenyl-SO₂—NH—C(=N—OCH₃)—NH—(triazine with 2 OCH₃)] | 173–175° C. |
| I-6 | [phenoxyphenyl-SO₂—NH—C(=N—OCH₃)—NH—(triazine with OCH₃ and CH₃)] | 141–144° C. |

TABLE 1-continued

| Compound No. | Structure | mp. |
|---|---|---|
| I-7 | [biphenyl-SO₂—NH—C(=N—OH)—NH—(triazine with 2 OCH₃)] | 202–204° C. |

EXAMPLE 8

Wettable powder

Fifteen parts of compound No. I-1 of the invention, 80 parts of a 1:5 mixture of powdery diatomaceous earth and powdery clay, 2 parts of sodium alkylbenzenesulfonate, and 3 parts of a sodium alkylnaphthalenesulfonate/formaldehyde condensate are pulverized and mixed to form a wettable powder. It is diluted with water and dropped onto weeds and/or their habitat.

EXAMPLE 9

Emulsifiable concentrate

Thirty parts of compound No. I-2 of the invention, 55 parts of xylene, 8 parts of polyoxyethylene alkyl phenyl ether and 7 parts of calcium alkylbenzenesulfonate are mixed with stirring to form an emulsifiable concentrate. It is diluted with water and dropped onto weeds and/or their habitat.

EXAMPLE 10

Dust

Compound No. I-3 of the invention (2 parts) and 98 parts of powdery clay are pulverized and mixed to form a dust. It is scattered over weeds and/or their habitat.

EXAMPLE 11

Dust

Compound No. I-4 of the invention (1.5 parts), 0.5 part of isopropyl hydrogen phosphate (PAP) and 98 parts of powdery clay are pulverized and mixed to form a dust. It is scattered over weeds and/or their habitat.

EXAMPLE 12

Granules

Water (25 parts) is added to a mixture consisting of 10 parts of Compound No. I-3 of the invention, 30 parts of bentonite (montmorillonite), 58 parts of talc and 2 parts of a lignosulfonate, and they are well kneaded. The mixture is processed by an extrusion-type granulating machine to form granules having a size of 10 to 40 mesh which are then dried at 40° to 50° C. to form granules. The granules are scattered over weeds and/or their habitat.

EXAMPLE 13

Granules

Ninety-five parts of clay mineral particles having a particle size distribution between 0.2 and 2 mm are put in a rotary mixer, and with rotation, 5 parts of compound No. I-1 of the invention dissolved in an organic solvent is sprayed onto the clay mineral particles to wet them uniformly. The particles are then dried at 40° to 50° C. to form granules. They are scattered over weeds and/or their habitat.

EXAMPLE 14

Test of stalk-foliar/soil treatment of aquatic paddy weeds in the watered state (pot test)

Preparation of an active compound

Carrier: 5 parts by weight of acetone

Emulsifier: 1 part by weight of benzyloxypolyglycol ether

A preparation containing the active compound is formed by mixing 1 part by weight of each of the active compounds with the carrier and emulsifier in the amounts shown above, and diluting a predetermined amount of the resulting emulsifiable concentrate with water.

Testing method

Aquatic paddy soil was filled in Wagner pots (1/5,000 ares), and rice seedlings (variety: Kinnampu) in the 2- to 3-leaf stage (plant height about 10 cm) were transplanted at a rate of 2 per pot. Seeds of *Monochoria vaginalis*, *Scirpus juncoides* and broad-leaved weeds, small fragments of *Eleocharis acicularis*, and tubers of *Cyperus serotinus*, and *Sagittaria pygmaea* were inoculated in the pots. The soil in the pots was maintained in the wet state. About 7 to 9 days after sowing, each pot was watered to a depth of about 6 cm. A predetermined amount of the compound of this invention in the form of an emulsion was applied by a pipette to treat each pot. After the treatment, the pots were watered for 2 days at a rate of 2 to 3 cm per day, and thereafter maintained in the watered state to a depth of about 3 cm. In the fourth week after treatment by the chemical, the herbicidal effect and the degree of phytotoxicity were evaluated on a grade of 0 to 5 as follows:

Evaluation of the herbicidal effect (the herbicidal rate based on the non-treated area)

5: at least 95% (withered)
4: at least 80% but less than 95%
3: at least 50% but less than 80%
2: at least 30% but less than 50%
1: at least 10% but less than 30%
0: less than 10% (no effect)

Evaluation of phytotoxicity to rice (the phytotoxicity rate based on the non-treated area)

5: at least 90% (fatal injury)
4: at least 50% but less than 90%
3: at least 30% but less than 50%
2: at least 10% but less than 30%
1: more than 0% but less than 10%
0: 0% (no phytotoxicity)

The results are shown in Table 2.

Table 2

| Compound No. | Amount of the active ingredient (kg/ha) | Herbicidal effect Weeds | | | | | | Phytotoxicity Rice |
|---|---|---|---|---|---|---|---|---|
| | | A | B | C | D | E | F | |
| I-1 | 0.5 | 5 | 5 | 5 | 5 | 4 | 5 | 0 |
| I-3 | 0.5 | 5 | 5 | 5 | 5 | 4 | 5 | 0 |
| I-4 | 0.5 | 5 | 5 | 5 | 5 | 4 | 5 | 0 |
| I-6 | 0.5 | 5 | 5 | 5 | 5 | 4 | 5 | 0 |
| I-7 | 0.5 | 5 | 5 | 5 | 5 | 4 | 5 | 0 |
| Comparison simetryn | 0.5 | 4 | 3 | 5 | 5 | 2 | 2 | 2 |

Note:

1. The compound numbers correspond to those given hereinbelow.

2. The symbols A, B, C, D, E and F in the column of Weeds represent the following weeds.

A: *Eleocharis acicularis*
B: *Scirpus juncoides*
C: *Monochoria vaginalis*
D: broad-leaved weeds (*Lindernia procumbens*, *Rotala indica*, *Elatine triandra*, etc.)
E: *Cyperus serotinus*
F: *Sagittaria pygmaea*

3. Comparison, simetryn (common name): 2,4-bis(ethylamino)-6-methylthio-1,3,5-triazine Active compounds of general formula (I) in accordance with this invention in addition to those given in Example 14 showed the same degree of excellent effect.

By the same testing method as in Example 14, the herbicidal effects of the compounds of general formulae (II) and (VI) which are novel intermediates of the invention were tested. The results are shown in Table 3.

Table 3

| Compound No. | Amount of the effective ingredient (kg/ha) | Herbicidal effect Weed | | | | | | Phytotoxicity Rice |
|---|---|---|---|---|---|---|---|---|
| | | A | B | C | D | E | F | |
| II-1 | 0.5 | 5 | 5 | 5 | 5 | 4 | 5 | 0 |
| VI-1 | 0.5 | 5 | 5 | 5 | 5 | 4 | 5 | 0 |

Note:

1. The compound numbers are the same as those given hereinabove.

2. The symbols in the column of Weeds are the name as in Table 2.

It will be appreciated that the instant specification and examples are set forth by way of illustration and not limitation, and that various modifications and changes may be made without departing from the spirit and scope of the present invention.

What is claimed is:

1. A substituted phenylsulfonyl guanidine of the formula

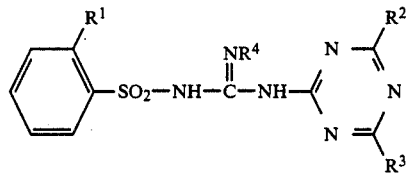

in which

R¹ is a phenyl or phenoxy group, each of
R² and R³ is a lower alkyl or lower alkoxy group, and
R⁴ is a hydrogen atom, a lower alkyl group or a lower alkoxy group.

2. A compound according to claim 1, wherein such compound is N-(2-biphenylylsulfonyl) N'-(4,6-dimethoxy-1,3,5-triazin-2-yl) N''-(methoxy)guanidine of the formula 3. A compound according to claim 1, wherein such compound is N-(2-biphenylylsulfonyl) N'-(4-methoxy-6-methyl-1,3,5-triazin-2-yl) N''-(methoxy)guanidine of the formula

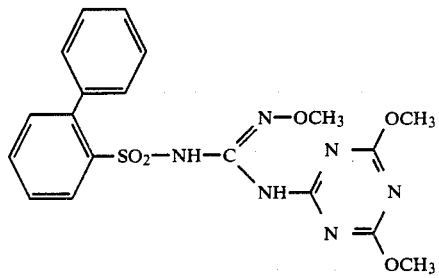

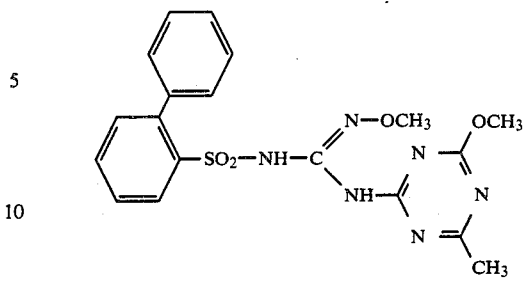

4. A herbicidal composition comprising a herbicidally effective amount of a compound according to claim 1 in admixture with a diluent.

5. A method of combatting unwanted vegetation which comprises administering to such vegetation or to a habitat where such vegetation is to be grown a herbicidally effective amount of a compound according to claim 1.

6. The method according to claim 5, wherein such compound is
N-(2-biphenylylsulfonyl) N'-(4,6-dimethoxy-1,3,5-triazin-2-yl) N''-(methoxy)guanidine or
N-(2-biphenylylsulfonyl) N'-(4-methoxy-6-methyl-1,3,5-triazin-2-yl) N''-(methoxy)guanidine
and is applied to rice or a locus in which rice is grown thereby selectively to kill weeds.

* * * * *